(12) United States Patent
Frazier et al.

(10) Patent No.: US 11,791,021 B2
(45) Date of Patent: *Oct. 17, 2023

(54) SYSTEM AND METHOD FOR BUILDING INTUITIVE CLINICAL TRIAL APPLICATIONS

(71) Applicant: Definitive Media Corp., Tustin, CA (US)

(72) Inventors: Jeff Frazier, Tustin, CA (US); John Reites, Tustin, CA (US); Sean Vassilaros, Tustin, CA (US)

(73) Assignee: Definitive Media Corp., Tustin, CA (US)

(*) Notice: Subject to any disclaimer, the term of this patent is extended or adjusted under 35 U.S.C. 154(b) by 39 days.

This patent is subject to a terminal disclaimer.

(21) Appl. No.: 16/716,976

(22) Filed: Dec. 17, 2019

(65) Prior Publication Data

US 2020/0202984 A1 Jun. 25, 2020

Related U.S. Application Data

(63) Continuation of application No. 15/644,603, filed on Jul. 7, 2017, now Pat. No. 10,510,438.

(51) Int. Cl.
*G16H 10/20* (2018.01)
*G16H 10/60* (2018.01)
*G06F 21/53* (2013.01)

(52) U.S. Cl.
CPC .............. *G16H 10/20* (2018.01); *G16H 10/60* (2018.01); *G06F 21/53* (2013.01)

(58) Field of Classification Search
CPC ........ G16H 10/20; G16H 10/60; G06F 21/53; G06F 8/60; G06F 9/445; G06F 11/34; G06F 11/3423; G06F 11/3438; G06F 11/3452

See application file for complete search history.

(56) References Cited

U.S. PATENT DOCUMENTS 6,640,231 B1 10/2003 Andersen et al.
8,140,318 B2 3/2012 Holland et al.
(Continued)

FOREIGN PATENT DOCUMENTS

WO WO 2017/062808 4/2017
WO WO-2017091360 A1 * 6/2017 ............ B60T 13/662

OTHER PUBLICATIONS

Bernal-Rusiel, Reusable Client-Side JavaScript Modules for Immersive Web-Based Real-Time Collaborative Neuroimage Visualization, May 1, 2017, frontiers in Neuroinformatics, vol. 11, Article 32, pp. 1-9. (Year: 2017).*

(Continued)

*Primary Examiner* — Christopher L Gilligan
(74) *Attorney, Agent, or Firm* — POLSINELLI LLP

(57) ABSTRACT

The present invention allows clinical trial organizers to operate a platform for creating trial specific custom mobile applications at a price point that would not be possible if the application were created by programmers on a trial-by-trial basis. The invention shortens build time by creating a hierarchy of questions that changes the next question posed to the user based upon their answer to a previous question thereby reducing the number of questions the user must answer while providing the application creation platform with the detailed information relevant to a specific clinical trial. The platform uses a simulation builder that provides a test version of the application to the user mobile device during the application creation process thereby allowing the user to see the layout of the application as they progress through the building process. While building the application, the user can create a simulated version of the application in real time deliver the same to the mobile device of the user. The system creates a handshaking process that allows the user to create annotations and/or edits in the simulated application that are communicated back to the building (Continued)

platform. Changes made in the simulated application will affect the landing page the user sees when returning to the building platform. The system will collect usability data from a clinical trial application on a plurality of trial subject and trial organizer mobile devices. The system can measure variables such as time on page, misentries, and missed selections of icons to determine common trouble spots for users. That data may be used to redesign the interface or process flow of the application to optimize usability

23 Claims, 11 Drawing Sheets

(56) References Cited

U.S. PATENT DOCUMENTS

| | | | |
|---|---|---|---|
| 8,813,028 B2* | 8/2014 | Farooqi | G06F 8/34 |
| | | | 717/107 |
| 9,851,968 B2* | 12/2017 | Straub | G06F 8/20 |
| 10,126,912 B2 | 11/2018 | Wang et al. | |
| 10,394,638 B1* | 8/2019 | Lay | G06F 11/3409 |
| 10,510,438 B2 | 12/2019 | Frazier | |
| 11,481,092 B2 | 10/2022 | Roy | |
| 2005/0063575 A1* | 3/2005 | Ma | G16H 30/40 |
| | | | 382/128 |
| 2010/0245286 A1 | 9/2010 | Parker | |
| 2014/0109046 A1 | 4/2014 | Hirsch et al. | |
| 2014/0115506 A1* | 4/2014 | George | G06Q 10/06 |
| | | | 715/764 |
| 2014/0129258 A1 | 5/2014 | Charlot et al. | |
| 2014/0189641 A1 | 7/2014 | Anderson et al. | |
| 2014/0215495 A1 | 7/2014 | Erich et al. | |
| 2014/0278536 A1 | 9/2014 | Zhang et al. | |
| 2015/0195179 A1 | 7/2015 | Skare et al. | |
| 2015/0254432 A1 | 9/2015 | Stumm et al. | |
| 2016/0125171 A1 | 5/2016 | Finken et al. | |
| 2016/0267238 A1 | 9/2016 | Nag | |
| 2016/0283676 A1* | 9/2016 | Lyon | G06Q 10/10 |
| 2016/0364531 A1 | 12/2016 | Kamalasan et al. | |
| 2017/0046487 A1 | 2/2017 | Tran | |
| 2017/0075664 A1 | 3/2017 | Dominick et al. | |
| 2018/0113782 A1* | 4/2018 | Valacich | G06F 11/3419 |
| 2018/0157467 A1* | 6/2018 | Stachura | G06F 8/34 |
| 2018/0210640 A1 | 7/2018 | Kumar et al. | |
| 2019/0012434 A1 | 1/2019 | Frazier | |
| 2021/0327545 A1 | 10/2021 | Frazier | |

OTHER PUBLICATIONS

Lui, Li-Min; "A New Software Development Methodology for Clinical Trial Systems", Feb. 25, 2013. Hindawi Publishing Corporation Advances in Software Engineering, pp. 1-13 (Year: 2013).
U.S. Appl. No. 15/644,603 Office Action dated Feb. 21, 2019.
U.S. Appl. No. 15/644,603 Final Office Action dated Feb. 15, 2018.
U.S. Appl. No. 15/644,603 Office Action dated Aug. 24, 2017.
Geifman et al., Opening clinical trial data: are the voluntary data-sharing portals enough?, 2015, BMC Medicine, pp. 1-3. (Year: 2015).
U.S. Appl. No. 16/825,881 Office Action dated Apr. 6, 2022.
U.S. Appl. No. 16/825,881 Office Action dated Mar. 7, 2023.
U.S. Appl. No. 16/825,881 Final Office Action dated Sep. 21, 2022.
U.S. Appl. No. 16/825,881 Final Office Action dated Aug. 7, 2023.

* cited by examiner

| Patient App #123 | Number of Data Points | Average Time Spent | Average Number of Clicks | Completion % |
|---|---|---|---|---|
| Question 1 | 25 | 0:41 | 3.2 | 84 |
| ... | | | | |
| Question n | 22 | 0:45 | 2.5 | 75 |
| Element 1 | 23 | 0:15 | 2.6 | 91 |
| ... | | | | |
| Element n | 20 | 0:21 | 4.2 | 92 |
| Screen 1 | 52 | 2:10 | 15.3 | 80 |
| ... | | | | |
| Screen n | 15 | 1:22 | 9.5 | 86 |
| Login 1 | 65 | 0:41 | 4.2 | 65 |
| ... | | | | |
| Login n | 14 | 0:32 | 3.0 | 95 |

FIGURE 10

| Application | Element 1 | Element 2 | Element 3 | Element 4 | Element 5 | Element 6 | ... | Element n |
|---|---|---|---|---|---|---|---|---|
| Patient App #123 | 1 | N/S | 4 | 3 | 2 | N/S | | 5 |
| Patient App #234 | N/S | 1 | 2 | 3 | 4 | 5 | | 6 |
| Patient App #345 | 5 | 3 | N/S | 1 | 4 | N/S | | 2 |
| Patient App #456 | 3 | 1 | 2 | 5 | N/S | 4 | | N/S |
| Patient App #567 | N/S | 5 | 4 | N/S | 3 | 2 | | 1 |
| Patient App #678 | 1 | 2 | 1 | 2 | 4 | 5 | | N/S |
| Patient App #789 | 4 | N/S | 5 | 4 | 3 | N/S | | 5 |
| Patient App #890 | 2 | N/S | 5 | 4 | 1 | 3 | | N/S |

FIGURE 11

SYSTEM AND METHOD FOR BUILDING INTUITIVE CLINICAL TRIAL APPLICATIONS

CROSS-REFERENCE TO RELATED APPLICATION

This application is a continuation and claims the priority benefit of U.S. patent application Ser. No. 15/644,603 filed Jul. 7, 2017, which is incorporated by reference herein in its entirety.

BACKGROUND OF THE INVENTION

Field of the Invention

The present invention generally relates to mobile applications. More specifically, the present invention concerns the creation of customized mobile applications for clinical trials without the need for extensive application programming knowledge.

Description of the Related Art

Various means for application testing or creation of a sandbox are known in the art. These prior art solutions suffer, however, from extended build times and lack of specificity concerning a given test or trial. Both also require extensive knowledge of software development and coding, skill sets that are often exclusive from the clinical testing realm, which has nevertheless become increasingly dependent upon mobile devices and application software running on the same. Prior art methodologies also require weeks if not months of development and are not scalable or flexible with respect to changes in demand or focus.

Mobile application testing is a process by which software applications developed for a handheld or other mobile devise are tested for functionality, usability, and consistency. Mobile application testing, however, suffers from a number of testing demands that are often not related to the needs of a clinical study. For example, typical mobile application testing involves not only functional testing, but laboratory testing, performance testing, memory leakage testing, interrupt testing, installation testing, certification testing, security testing, location testing, OST, and load testing. While potentially useful information in some environments, this information is less germane to a clinical test application.

Sandboxes on the other hand are testing environments that isolate untested code changes and experimentation the production environment or code repository. Sandboxing protects live servers and data from instances where reversion because of a build error may be difficult to effectuate. Sandboxing is ineffective, however, because it replicates minimal functionality needed to accurately test an application or code under development. In many instances, this minimal realm of operability is not sufficient to effectuate or understand whether a clinical testing application is ready for release, achieves a desired purpose, engages a user, or even operates in conjunction with a mobile device.

There is a need in the art for systems and methods related to improved application creation platforms. This need includes creating engaging user experiences, end-to-end technology suites, and turn-key solutions that allow for successful remote patient and clinical research studies. The need further includes intuitive design configuration, easily reviewed, approved, and scheduled study launches, and accessing and extracting data and study performances in real time. All of this would ideally occur in a context comprehensible to individuals or professionals that are not software and hardware engineers but that nevertheless need access to hardware and software applications designed for their specific needs.

SUMMARY OF THE CLAIMED INVENTION

In a first claimed embodiment of the invention, a method for remote clinical trial organization is recited. In the method, a response is received for at least a first question designed to identify one or more elements necessary to complete a clinical trial in an application based testing environment. A second question is posited based on at least a received response for the at least first question, whereby the responses to the at least first and second question are used to access a database of elements for constructing the application for the clinical trial application. These elements include clinical and consumer medical monitoring devices relevant to the trial. Data collected from a trial subject is processed utilizing the application for the clinical trial and any corresponding clinical and consumer medical monitoring devices. The application is authored by a software platform operating in conjunction with the clinical trial. The clinical trial application is modified responsive to the processed data collected from the trial subject.

In a second claimed embodiment of the invention, a system for building a clinical trial application is recited. The system includes a user device for providing clinical trial requirements and a software platform executing to posit a series of iterative questions that drive building the clinical trial application in accordance with the clinical trial requirements. A response to each question determines a next posited question in the series. The clinical trial application is built in real-time and responsive to the posited series of iterative questions. The clinical trial is then simulated in real-time and launched to user devices. Data is received from the user devices and captured by the clinical trial application, which may be modified responsive to the received data captured by the clinical trial applications.

BRIEF DESCRIPTION OF THE DRAWINGS

FIG. 10 illustrates a usability database.

FIG. 11 illustrates a building database.

DETAILED DESCRIPTION

Systems and methods for application creation platforms are disclosed. These platforms allow for the creation of engaging user experiences with an end-to-end technology suite and turn-key solutions. The disclosed invention allows for intuitive design configuration, the review, approval, and scheduling of study launches, and accessing and extracting data and study performances in real time. The overall end-result is successful remote patient and clinical research studies. The studies may utilize advanced tokenization techniques that are compliant with data security requirements that are HIPPA and FDA approved. The current disclosed platform may likewise be integrated into existing data systems that are scalable while remaining customer configurable to suit the individual needs of a given study or user.

Figure 1:
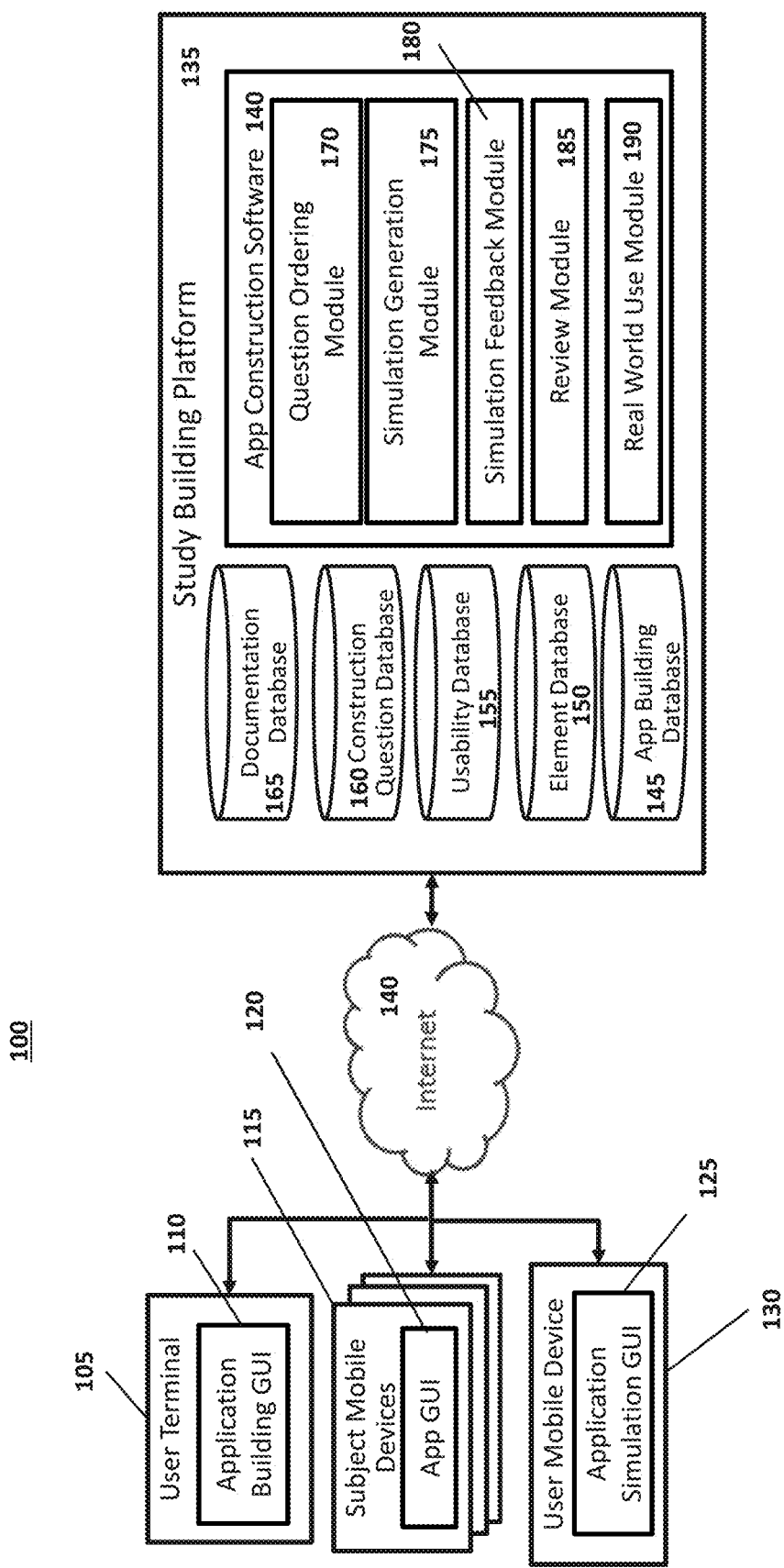
FIG. 1 illustrates a system for creation of applications for clinical trials.

FIG. 1 illustrates a system 100 for creation of applications for clinical trials. The system 100 of FIG. 1 further allows for organizing and reporting in compliance with various privacy and regulatory requirements that may pertain to the administration of a particular clinical trial (e.g., HIPPA or the FDA). The system 100 of FIG. 1 includes a user terminal 105 with an application building interface 110, subject mobile devices 115 with application interfaces 120, a user mobile device 125 with an application simulation interface 130, and a study building platform 135.

Platform 135 and the aforementioned terminal 105 and devices 115 and 130 may be communicatively coupled over a communications network 140 such as the Internet. Communications network 140 may not necessarily be limited to the Internet. Network 140 may include any number of local-area and wide-area networks, open- and proprietary-networks, wired and wireless networks, and networks that may or may not be subject to encryption or the use of VPNs or tunneling.

It should further be noted that in various implementations, platform 135 and terminal 105 and devices 115 and 130 may not be communicatively coupled at the same time. For example, in some instances only terminal 105 may be connected to platform 135 while at other times only subject mobile devices 115 may be connected to platform 135. In other examples, a single subject mobile device 115 may be communicatively coupled to the platform 135 whereas multiple such devices 115 may be connected at others. All of the aforementioned terminals and mobile devices include requisite computing componentry such as processors, memories, and communications interfaces to allow for receipt, transmission, and processing of data such that it may be displayed, accessed, and manipulated through the appropriate GUI and other input/output devices and/or utilized by platform 135.

The study building platform 135 facilitates generation of applications that allow for user engagement as part of an overall end-to-end technology suite that can provision a complete product or service ready for use as part of a turn-key solution. Platform 135 may be integrated into an existing data system such that the system 100 is scalable while remaining customer configurable. In this way, the individual needs of a given study or user may be readily facilitated. Platform 135 may further facilitate privacy and data security compliant studies as may be required by the likes of HIPPA and the FDA by utilizing advanced tokenization techniques whereby a sensitive data element may be substituted with a non-sensitive equivalent that has no extrinsic or exploitative value.

Platform 135 as illustrated in FIG. 1 includes application construction software 140. Platform 135 further includes an application building database 145, application element database 150, usability database 155, construction question database 160, and documentation database 165. Construction software 140 as illustrated in FIG. 1 includes a suite of modules, including question ordering module 170, simulation module 175, feedback module 180, review module 185, and real-world use module 190. It should be noted that embodiments of the invention may in some instances include all of the modules. In other instances, fewer modules may be included. Similarly with databases as various embodiments may use all or fewer of the databases currently illustrated in FIG. 1. Further, embodiments of the present invention may combine the functionality of certain application modules and/or databases into singular operating databases or modules. Platform 135 also envisions the presence of any requisite computing componentry such as processors, memories, and communications interfaces to allow for receipt, transmission, and processing of data such that it may be displayed, accessed, and manipulated through the appropriate GUI and other input/output devices and/or utilized by terminal 105 and devices 115 and 130.

The building database 145 includes completed applications, third-party applications, and storage for applications under construction. Applications stored in database 145 may be used as foundations for future applications or to provide design studies or context for the same. Various ancillary third-party applications offering different functionalities may likewise be stored in said database. In progress applications may be maintained here in the event that an application is not completed or further queries or real-world data are required to complete the build or further instantiation of the same.

The application element database 150 includes the necessary data and componentry necessary to build a mobile, tablet, or other patient device application. Database 150 includes the core elements of a software or mobile application that may instantiate further aspects or builds of the application whereby code is effectively writing more code. As a result of information maintained by database 150, an application effectively 'builds' itself based on various requirements of the application as may be identified from information provided by or accessed from construction software 140 and or databases 155-165.

Patient devices are inclusive of wearable devices and other mobile patient monitoring technology that may be worn, carried, implanted, or otherwise transported by a patient. Such hardware may communicate with a tethered mobile device such as subject mobile devices 115 or other transmitting device through known communications protocols. That device may, in turn, communicate with platform 135. In some instances, the patient monitoring device may be the mobile device 115.

Usability database 155 stores real-world usage data collected from subject mobile devices once an application has been built in conjunction with element database 150. While illustrated as a part of platform 135, this database may be maintained by a third-party or at a secure offsite location to comply with certain privacy or statutory requirements. Construction question database 160 contains questions used by the question ordering module 170 to guide the creation of the application in conjunction with element database 150. The question ordering module determines those elements in the element database 150 that should be used in conjunction with element database 150 based upon answers to posited questions.

The user administering a clinical trial and building an application corresponding to the same accesses system 100 and platform 135 from (for example) the user terminal 105, which may be a personal computer. Terminal 105 may be directly connected to platform 135 through a local area network connection. Platform 135 may alternatively be cloud-based or a SAAS application that instantiates from a server farm on an as needed basis.

The construction software 140 of platform 135 commences execution when the user logs in with proper credentials. Software 140 calls question ordering module 170, which will select a series of questions from construction question database 160 and that are presented to the user by way of interface 110. Each 'next question' is presented based on the answer to a previous question or a series of questions such that various components, features, and documentation (as may be maintained by database 165) are ultimately integrated into the study application by way of a catalog of application and back-end databases necessary or ancillary advantageous to the needs of a given study. The answers to these questions will determine which elements and modules are drawn from the element database 150 and building database 145 to finally construct the clinical trial application. This may include substantive features such as patient data collection as well as more cosmetic features such as application content and layout. In some instances, it is envisioned that the layout may drive the quality of patient feedback thus causing the cosmetic aspects to become hybrid substantive features.

The simulation generation module 175 creates a simulation of the application based upon the results of the question ordering module 170, the build from element database 150 and, as needed, application building database 145. That simulation is sent to the mobile device 125, which may be a secure mobile device for real-world testing of clinical trial applications. User device 130 may be 'locked down' or have certain security functions installed to maintain the security or control of the yet-to-be-released clinical trial application, including a simulation GUI 130 that may allow for controlled input of output differing from a real-world interface like that found on devices 115 and corresponding GUI 120.

Application software 140 of building platform 135 runs the simulation feedback module 180, which polls the application simulation GUI 130 on device 125 for a user test-selection. When the user selects an element in the simulation, the element database 150 is queried to identify the possible changes that can be made to that component of the application or trial. These changes may include removing or replacing application elements, changing the color of the elements, changing the arrangement of the elements as well as tracking or collection of certain data from various resources or hardware components or otherwise software applications that may ultimately be present on a user device like subject mobile device 115. Those options and the results of any changes may be displayed for the user on GUI 125 or, alternatively, at terminal 105 and GUI 110, which may run in parallel with device 125 during the build stage.

When the user selects which type of modification they wish to make by way of interface 125, the further options or output from that modification are likewise displayed such that a user has a real-time understanding of changes to the application and potential study results. Once the edit has been selected, the option to end edits is displayed for the user. If the user selects the end edits option the simulation feedback module 180 ends its execution and returns control of the build to the construction software 140. The user can continue to select elements as they navigate through the ordering module 170, corresponding simulations as generated by simulation generation module 175, and simulation feedback from module 180, which tracks revisions to the application study.

Once the user completes the application simulation on a test mobile device, the user returns to the application building interface 110 on the user terminal 105. The user will then be moved into the review phase of the application and clinical trial build as driven by review module 185. Module 185 will execute to walk a user through a process to review their study, determine any gaps or recommended areas to address, and provide a scan of their study to confirm all required elements/sections are completed as may be required by various industry, clinical, or other scientific standards. Based on the previous selections by the user, the system identifies all third-party or extraneous applications and hardware that may or must provide data relevant to the study.

A list of applicable or available user mobile devices (115) is then presented to the user on the application building interface 110. Specialized or study specific clinical devices may be sourced and distributed to trial subjects. Consumer devices such as iPhones, wearables, or other health tracks may be allowed by the study organizer depending on the nature of the clinical study. In these cases the trial subject will be presented with the list of allowed consumer devices thereby allowing for provisioning data directly through the built and installed clinical trial application to the study platform. This section also provides the user with automated documentation (e.g., IRB/EC submission information, project plans, and business cases) from database 165 that may be necessary to conduct or facilitate the study.

The end of the review module 185 execution allows the user to approve the launch of the application. If the user does not approve the application for launch, the system reverts to the question ordering module 170 for potential further application development. When the user decides the application is ready to be published for download or installation by subjects or supervisors in the clinical trial, the platform then directs the user to a study portal (not shown) providing status on their submissions and completed launch. Upon approval by a distribution platform (e.g., an application store for a potential mobile community) or installation for clinical devices, data begins to flow through the portal providing research information, patient progress, and analytics. That data may be maintained by platform 135 in usability database 155 or in a secure database, which may be maintained by a patient, study site, hospital, university, or other third-party provider.

Construction software 135 then begins polling for real world application usage by way of module 190 from any mobile devices 115 hosting the application and providing data. When real world application usage data is available as determined by such polling, the usability database 155 will be updated with the new information. Polling may be on-demand, scheduled, random, or event-based with respect to some occurrence on a user device 115 or based on network conditions at the platform 135.

In an exemplary and non-limiting analysis of use data, for each screen/element/question/login/prompt that is accessed on a subject mobile device 115 the usage data will be recorded, which may include information such as the time spent on that element, the number of clicks on that element and if the subject completed or abandoned that element. The usability database 155 will have the average for each of these measures and more for each such screen/element/question/login/prompt and the number of data points it has been provided to calculate those averages as well as other data that may be passively recorded by the device.

A first value stored in database 155 is examined by the use module 190, which may be the completion percentage for a particular screen/element/question/login/prompt. If the completion percentage is below a user defined threshold, such as 70%, an alert is sent to the user as this screen/element/question/login/prompt is apparently causing an unacceptable number of trial subjects to not complete that portion of their assessment. This alert can be sent in a variety of ways, including text or email, but will include, or include a link to, a report about the real world usage and a link to the portion of the question ordering module 170 that relates to the screen/element/question/login/prompt that had the unacceptably low completion percentage.

If the completion percentage is above the user defined threshold, a next value is examined, which may be the average time to complete the screen/element/question/login/prompt. If that is below a user defined threshold, the system returns to the construction software 140 and polls for more real world usage data. If the average time to complete is above the threshold the number of data points that were used to produce this average time to complete is examined to determine if the sample size is large enough. If the number of data points is below a preset threshold for sample size the system returns to the construction software and polls for more real world usage data.

If the sample size is large enough for the data to be meaningful, the number of elements on the problem screen is examined. If the number of elements on the screen is above a user defined threshold the elements are split into two screens and the system returns to the construction software 140 and polls for more real world usage data. If the number of elements does not exceed the threshold, the location and sequence of the clicks subjects made on that screen are examined. The order and location of those clicks are then used to rearrange the elements on the screen so that the order in which they are designed to be completed matches the most frequent order and location of the real world clicks.

If the click locations are not indicative of a layout problem—for example there is no clear pattern in the real world clicks—the system sends an alert to the user similar to the alert sent when the completion percentage drops below the acceptable threshold. In both cases, either after the alert or after the elements is rearranged on the screen, the system 100 returns to the construction software 140 and polls for more usage data.

Figure 2:
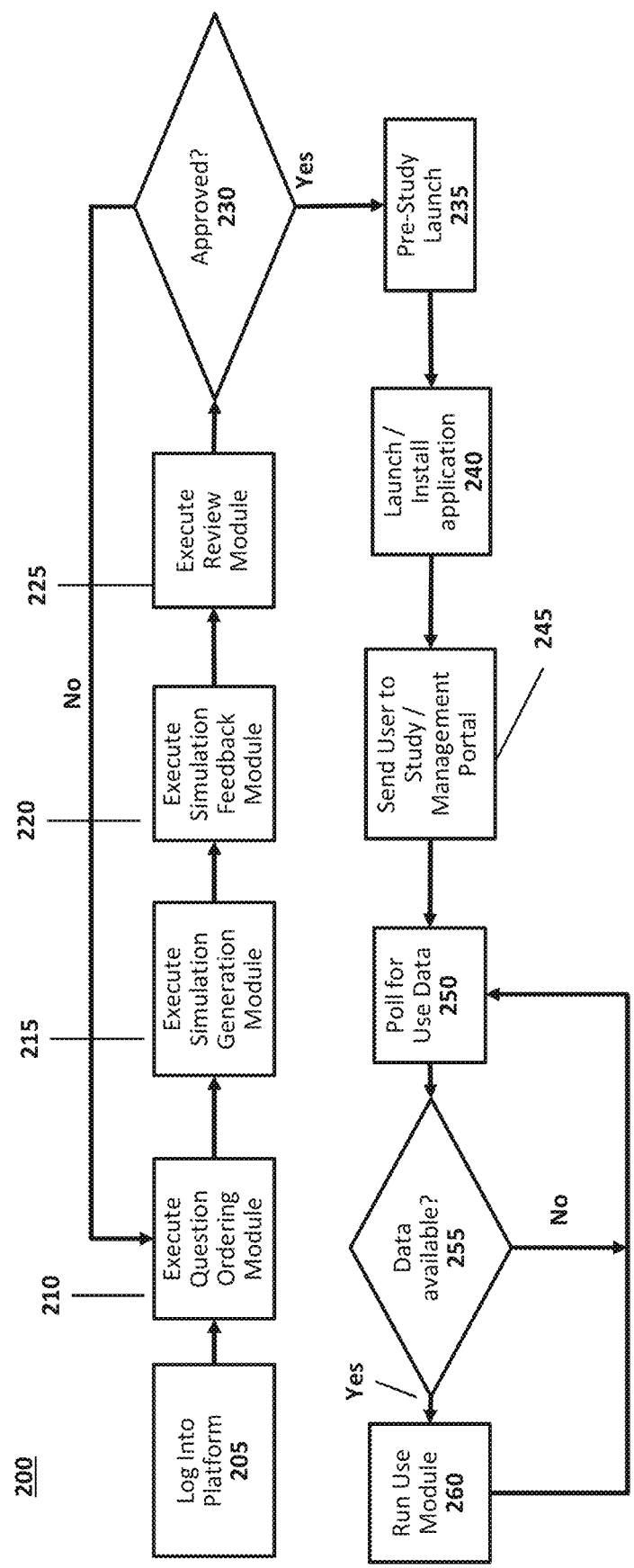
FIG. 2 illustrates a workflow for application construction software.

FIG. 2 illustrates a workflow 200 for application construction software 140. Software 140 and corresponding workflow 200 may be used in the context of the system 100 illustrated in FIG. 1. The construction software commences execution when the user logs in at step 205. Question ordering module executes at step 210. This module—as discussed in the context of FIG. 1—will select the next question from the construction question database based on the answer to a previous question. The answers to these questions will determine which elements and modules are drawn from the element and other databases to construct the application for a clinical trial. In this fashion the application content and layout will be determined as will various data acquisition functionalities.

Next, the simulation feedback module creates a simulation of the application based upon the results of the question ordering module at step 215. That simulation is sent to the user mobile device and the construction platform runs the simulation feedback module at step 220. Once the user is done with the simulation interface on their mobile device, the user returns to the application building interface on the user terminal. The user will then be moved into the review module, which executes at step 225.

This module will walk the user through a process to review their study, determine any gaps or recommended areas to address, and provide a scan of their study to confirm required elements/sections are completed. This section also provides the user with their automated documentation supporting their other required processes. The end of the review module allows the user to approve the launch of the application at step 230. If the user does not approve the application for launch, the system reverts back to the question ordering module at step 210. When the user decides the application is ready to be published for download by subjects or installation on devices in the clinical trial, the platform then directs the user to the study portal (not depicted) at step 235 to provide an anticipated launch date, evidence of legal authority to commence the study, and any other institutional or board approval required for the same.

Upon store or install approvals, the application is installed at step 240. Data will ultimately flow through a portal providing clinical study data, patient progress, and analytics such as future machine learning and artificial intelligence on the generated data; management of said data may occur at step 245. This portal is where the study is managed for the customer and includes major aspects of the study such as documentation, timeline, prototype download, and schedule of events. The application construction software will also poll for real world usage at step 250 from any mobile devices that downloaded the application at step 240. When real world application usage data is available the application construction software will launch the real world application use module 255 to provide that analysis as described in the context of FIG. 1.

Figure 3:
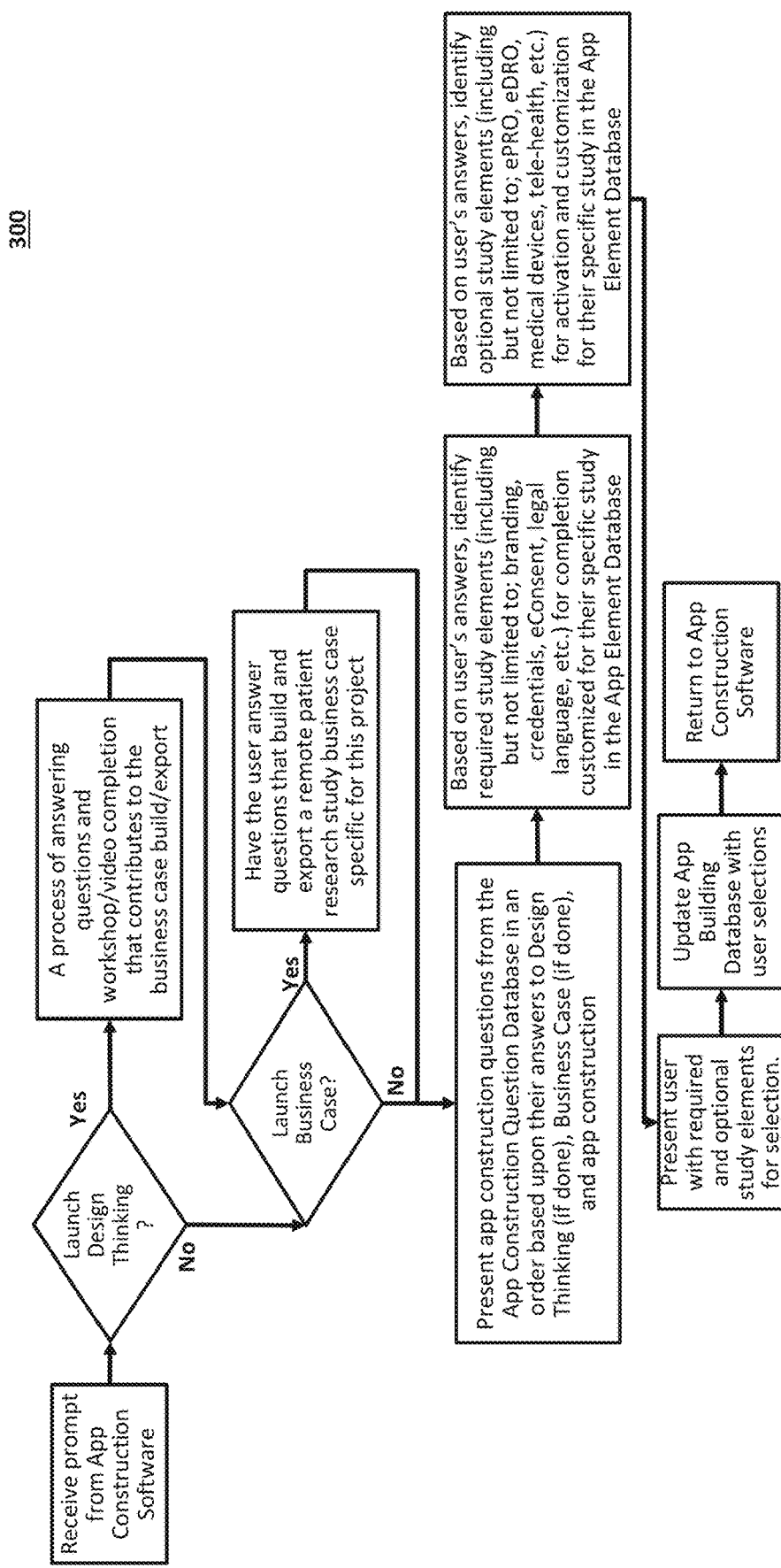
FIG. 3 illustrates a workflow for a question ordering module.

FIG. 3 illustrates a workflow 300 for a question ordering module. The question ordering module takes the questions from the construction question database and poses them to the user in an order based upon the answers to previous questions. Before presenting the user with questions specifically related to application construction, the system offers the user two optional question sections: the design case and the business case.

If the user goes through the design section, the system will take them through a process of answering questions and workshop/video completion that contributes to the business case build/export. The user can then go through the business case section, during which they will have the opportunity to answer questions that build and export a remote patient research study business case specific for a project. After the two optional modules, the user will go through the construction specific questions, which are not optional. Based on answers and the identification of required study elements, including but not limited to branding, credentials, eConsent, and legal requirements, and completion of queries customized for the specific study as well as identification of optional study components such as ePRO, eDRO, medical devices, and tele-health, the user is presented with the required and optional elements for their study. Selections update the building database and the system executes construction software.

Figure 4:
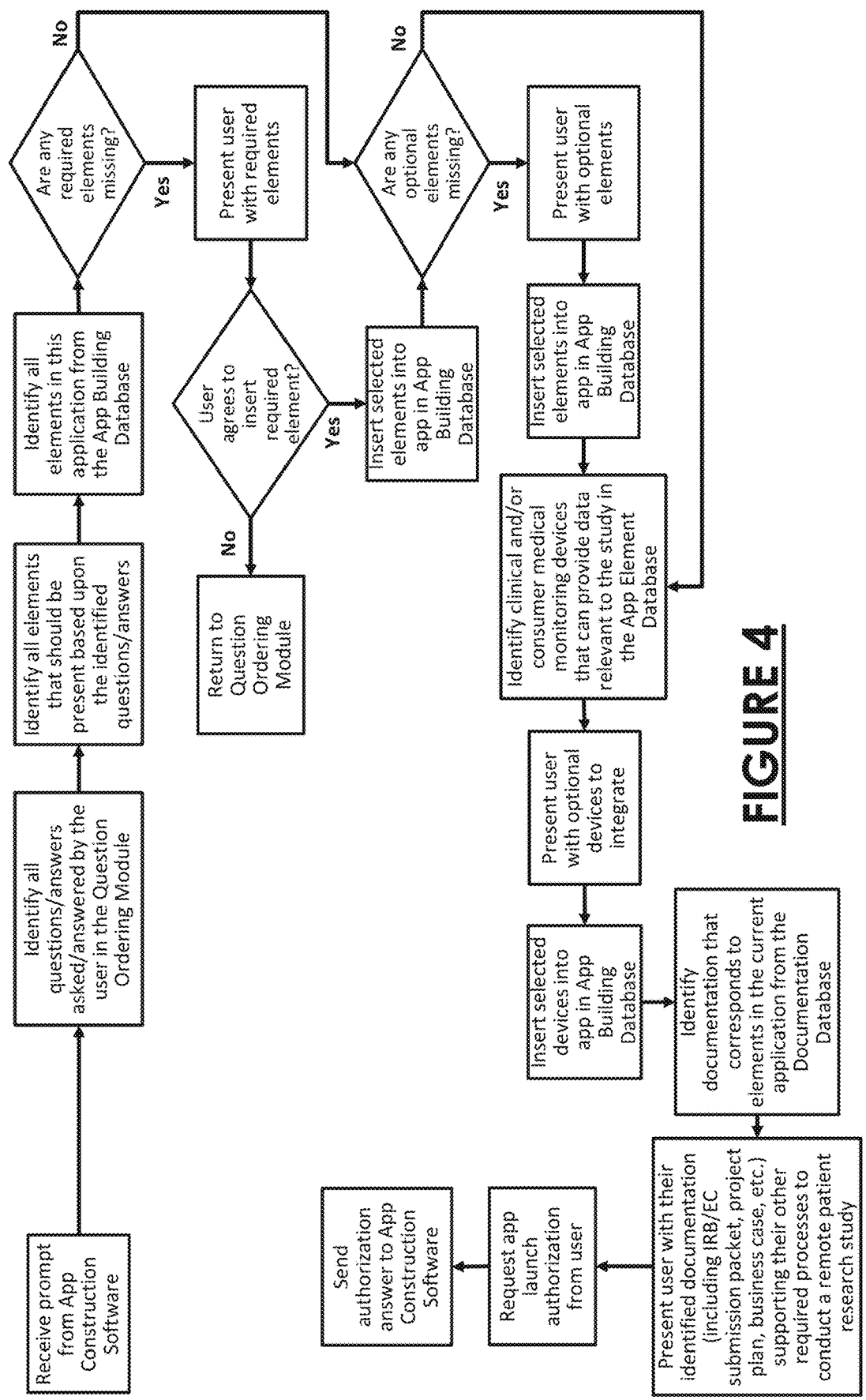
FIG. 4 illustrates a workflow for a review module.

FIG. 4 illustrates a workflow 400 for a review module. The review module walks the user through a process to review their study, determine any gaps or recommended areas to address, and provide a scan of their study to confirm all required elements/sections are completed. The workflow begins by identifying all questions/answers that were asked and answered by the user in the question ordering module. The elements that should be present based upon the questions asked and the answers given are then identified as this information is in the application element database. That list of elements is then compared to the elements that are in the current application in the application construction database. If there are any required elements missing, they are presented to the user. If the user agrees, the required elements are introduced into the application. If the user does not agree with the suggestion, the system will return to the question ordering module.

Optional elements that should be present based upon the question ordering module are then presented to the user. Optional elements that the user selects are then inserted into the application in the application building database. Based on all of the previous selections by the user, the system identifies ancillary devices and hardware such as clinical and consumer medical monitoring devices, smart watches, activity monitors, and blood glucose meters that can provide data relevant to the study from the application element database. The identified list of devices is then presented to the user on the application building interface. Clinical devices are sourced and distributed by the system to trial subjects. Consumer devices are allowed by the study organizer. In these cases the trial subject will be presented with the list of allowed consumer devices, and they can opt in to allow the data to be fed directly through the clinical trial application to the study platform.

The document database is then examined to identify documentation that corresponds to the elements in the application. The user is then presented with the identified documentation such as internal review board and ethics committee submission packets, project plans, business cases, and the like supporting the required processes to conduct a remote patient study. The user is then given the opportunity to approve the launch of the application. The user decision is then sent back to the app construction software.

Figure 5:
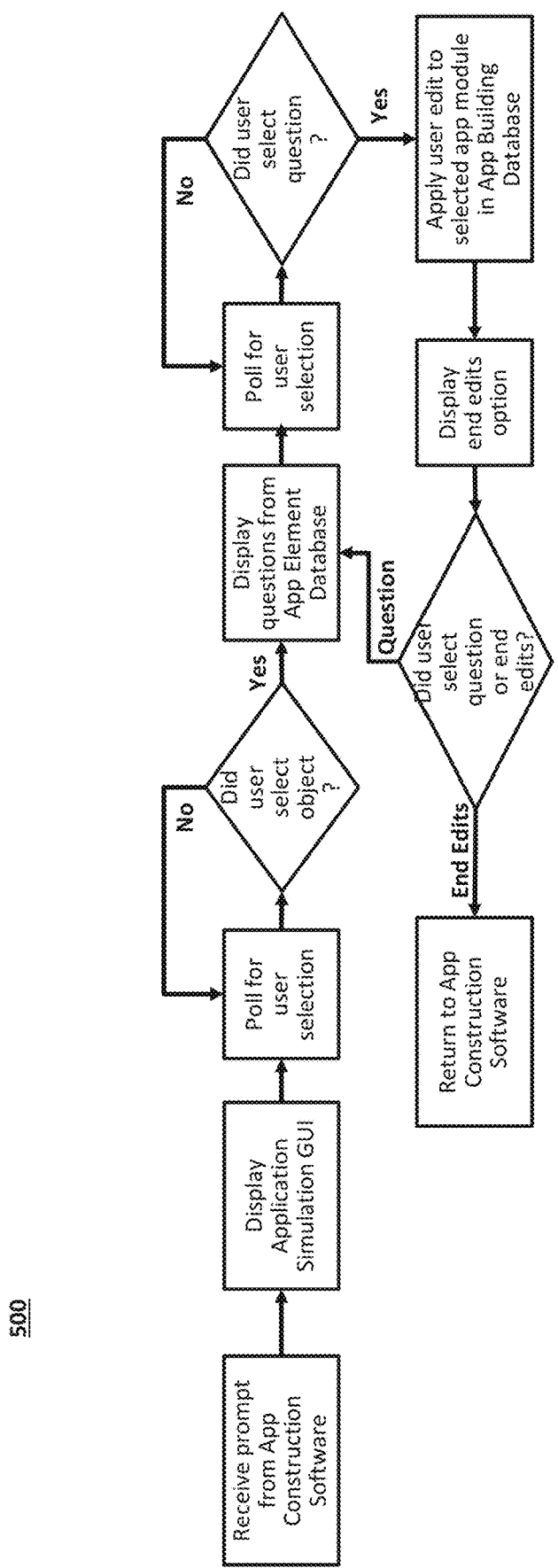
FIG. 5 illustrates a workflow for a simulation feedback module.

FIG. 5 illustrates a workflow 500 for a simulation feedback module. The simulation feedback module creates a simulation of the application based upon the results of the question ordering module. That simulation is sent to the user mobile device and the application construction platform runs the simulation feedback module. The simulation feedback module polls the application simulation for a user selection. When the user selects an element in the simulation, the application element database is queried to identify the possible changes that can be made to that element, including but not limited to, removing or replacing the element, changing the color of the elements, or changing the arrangement of the element. When the user selects which type of modification they wish to make, the options for that modification are displayed on the application simulation interface.

Once the edit has been selected the option to end edits is displayed for the user. If the user selects the end edits option the execution of the simulation feedback module ends and returns to the application construction software. The user can continue to select elements as they navigate through the application simulation and the simulation feedback module will continue to allow them to edit or rearrange their application.

Figure 6:
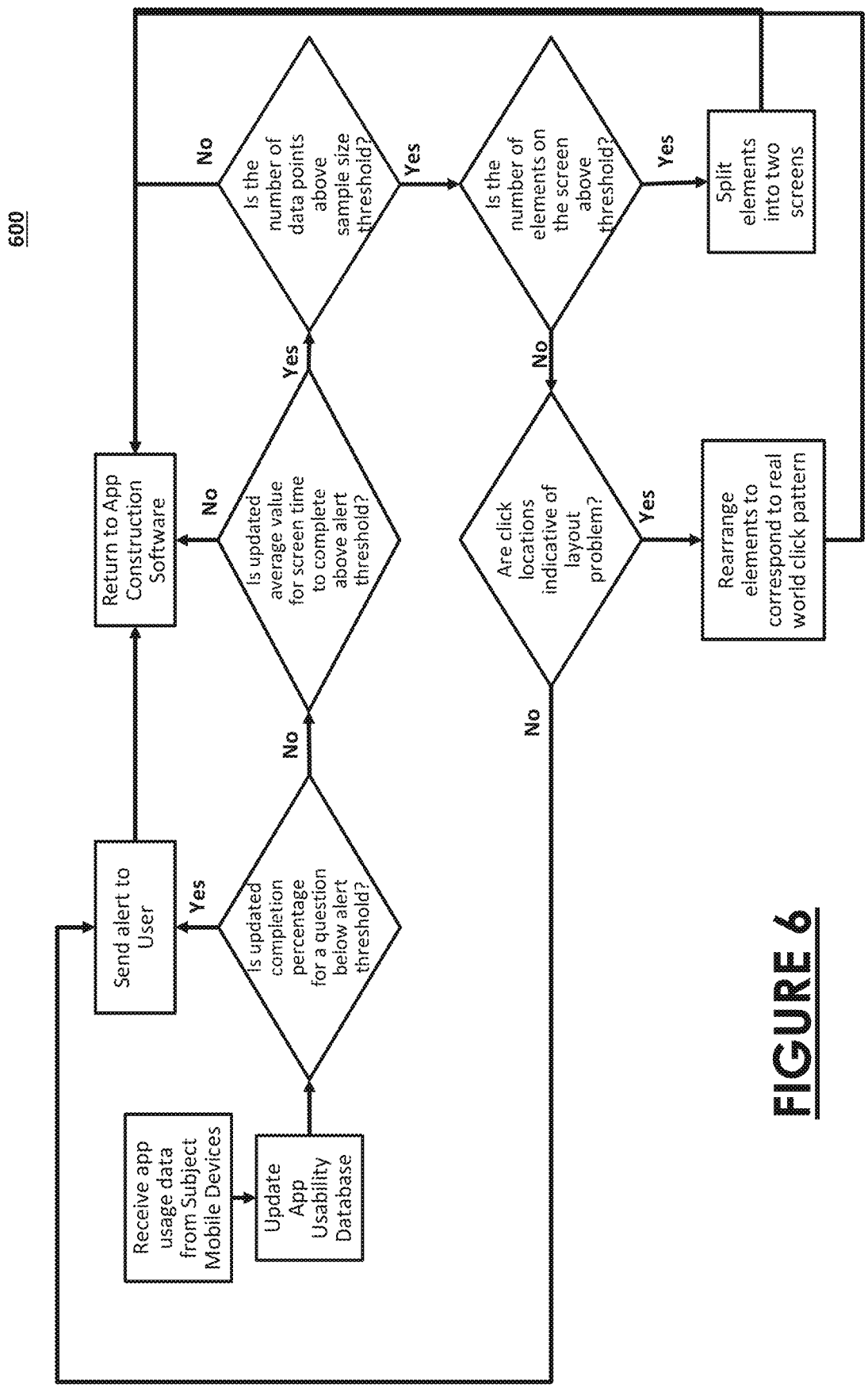
FIG. 6 illustrates a workflow for a use module.

FIG. 6 illustrates a workflow 600 for a use module. The use module executes when it receives application usage data from subject mobile devices. The usability database will be updated with the new information. For each screen/element/question/login that is accessed on a subject mobile device, the usage data may include the time spent on that element, the number of clicks on that element and if the subject completed or abandoned that element. The application usability database will have the average for each of these measures for each screen/element/question/login and the number of data points it has been provided to calculate those averages.

The first value that is then examined by the real world use module is the completion percentage for the screen/element/question/login in question. If the completion percentage is below a user defined threshold, in this example 70%, an alert is sent to the user as this screen/element/question/login is causing an unacceptable number of trial subjects to not complete that portion of their assessment. This alert can be sent in a variety of ways, including text or email, but will include, or include a link to, a report about the application usage data and a link to the portion of the question ordering module that relates to the screen/element/question/login that had the unacceptably low completion percentage.

If the completion percentage is above the user defined threshold, the next value examined is the average time to complete the screen/element/question/login. If that is below a user defined threshold, the system returns to the construction software and polls for more real world usage data. If the average time to complete is above the threshold the number of data points that were used to produce this average time to complete is examined to determine if the sample size is large enough. If the number of data points is below a preset threshold for sample size the system returns to the construction software and polls for more real world usage data.

If the sample size is large enough for the data to be meaningful the number of elements on the problem screen is examined. If the number of elements on the screen is above a user defined threshold the elements are split into two screens and the system returns to the app construction software and polls for more real world app usage data. If the number of elements does not exceed the threshold, the location and sequence of the clicks subjects made on that screen are examined. The order and location of those clicks are then used to rearrange the elements on the screen so that the order in which they are designed to be completed matches the most frequent order and location of the real world clicks. If the click locations are not indicative of a layout problem, for example there is no clear pattern in the real world clicks, the system sends an alert to the user similar to the alert sent when the completion percentage drops below the acceptable threshold. In both cases, either after the alert or after the elements are rearranged on the screen, the system returns to the construction software and polls for more real world usage data.

Figure 7:
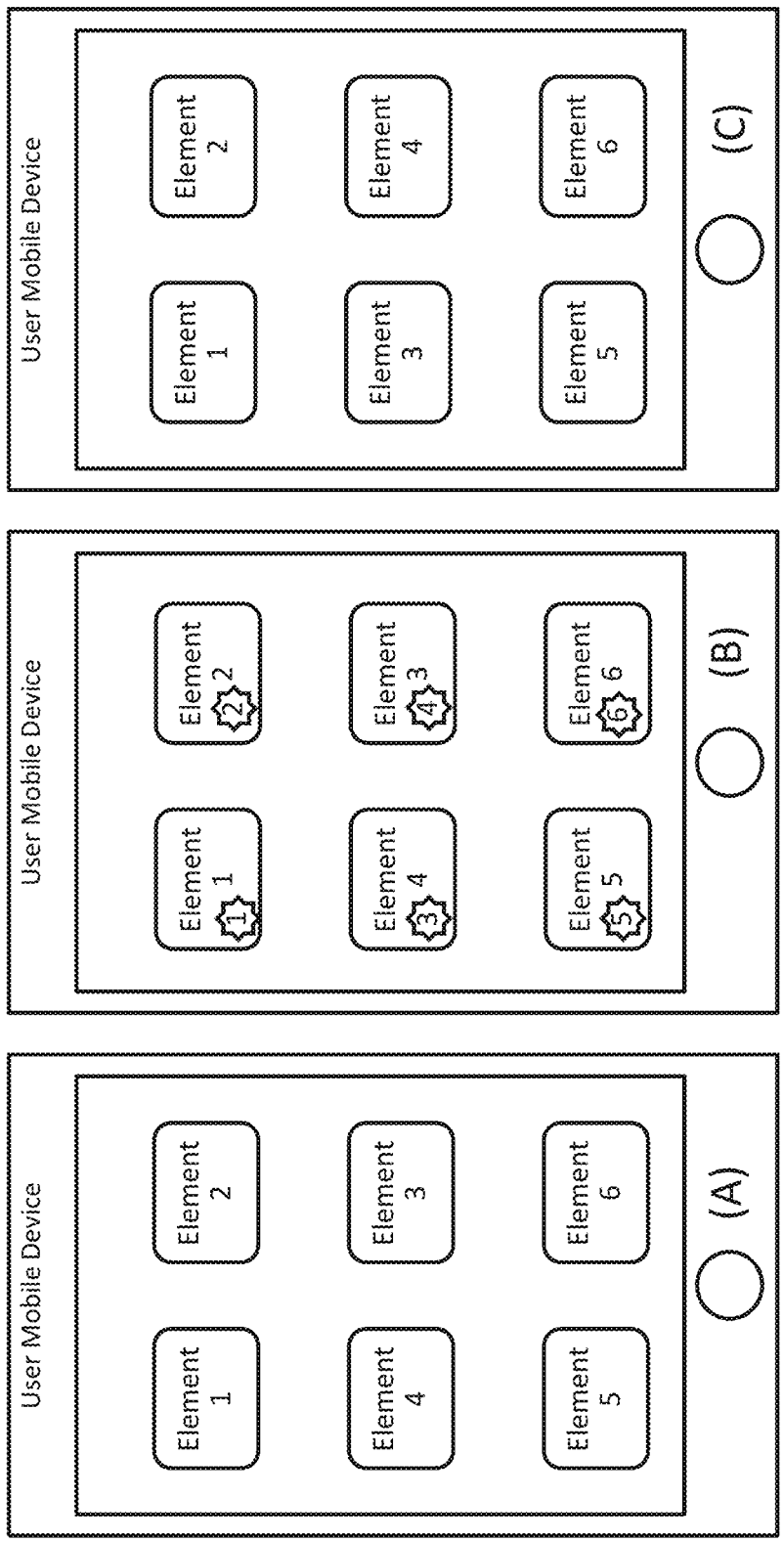
FIG. 7 illustrates exemplar mobile device interactions in the context of a use module.

FIG. 7 illustrates exemplar mobile device interactions in the context of a use module. More specifically, FIG. 7 represents the process in the real world use module that analyzes the clicking patterns of clinical trial subjects in order to better arrange the elements on the screen. Illustration (A) shows the original arrangement of the elements on the screen where they are numbered to represent the order in which they are meant to be completed. The numbered stars in illustration (B) show the click location and order. Illustration (C) shows the elements rearranged to coincide with the click pattern being observed in the real world.

Figure 8:
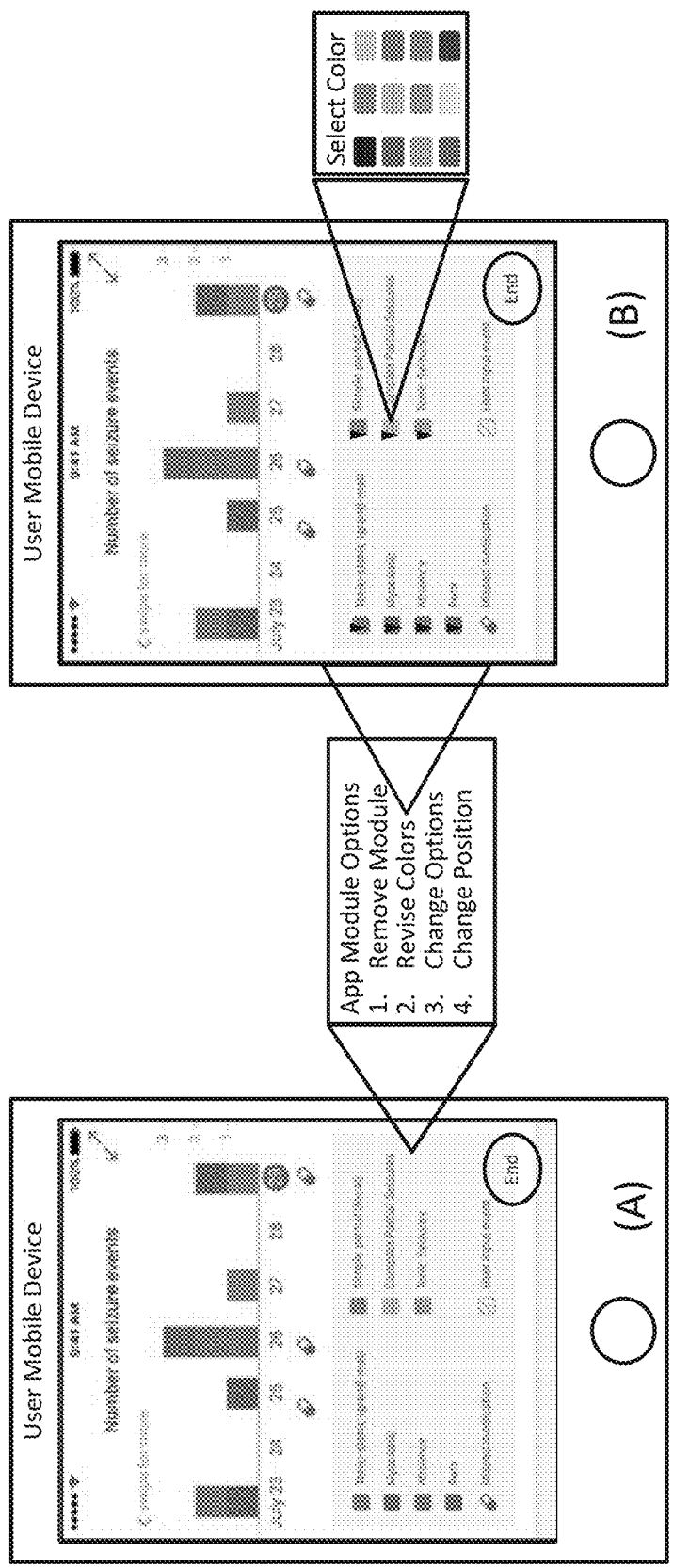
FIG. 8 illustrates an application simulation interface.

FIG. 8 illustrates an application simulation interface. Illustration (A) shows the screen as it has been designed in the construction software. In this example the user has selected the middle section to revise. The module options from the element database are displayed. In this case, the user can remove the module, revise the colors, change the options or change the position of the element on the screen. Different elements will have different questions, for example a text question may allow the user to reword the question. In this example the user has selected revise colors. Illustration (B) shows each of the color boxes now with a drop down menu. The user has selected the yellow color to change and their available options are displayed. At any point the user can select the "End" button which will prompt the construction software to get user approval to launch the application availability. The user can continue to navigate through the simulation making as many edits as they like before selecting the "End" button.

Figure 9:
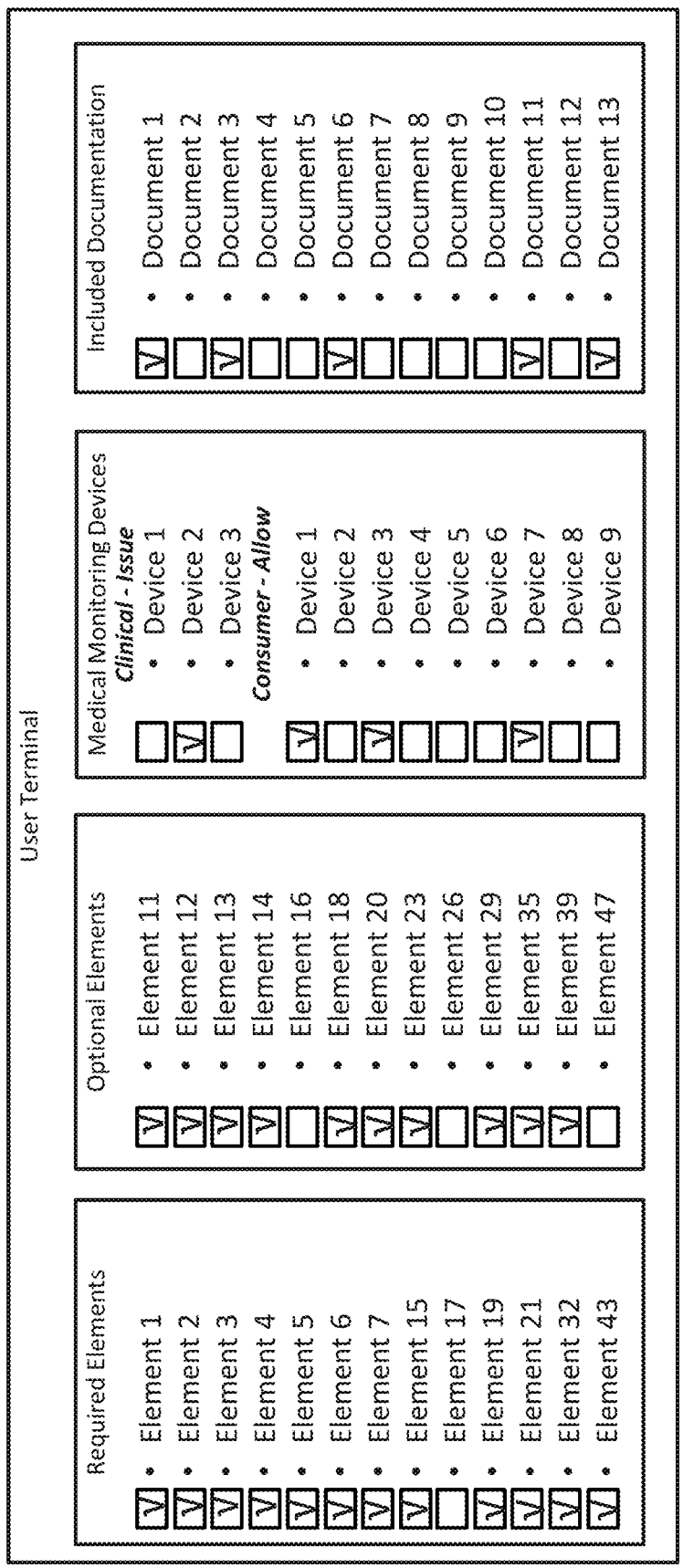
FIG. 9 illustrates an application review interface.

FIG. 9 illustrates an application review interface. More specifically, these figures represent the review module screen of the application building interface on the user terminal. The first box on the left list the elements determined to be required for the study by the construction software. Each element has a selectable box that allows the user to select to include or not include a given element. In this example the user deselected required element 17. This would take the user out of the review module and back to the question ordering module. The study cannot be launched without all required elements, so the user will need to either adjust the parameters of the study in the question ordering module or include the required element(s).

The second column contains all relevant elements that are optional. The third box shows the list of clinical or consumer medical monitoring devices that can provide data relevant to the study. In this example the user selected clinical device 2. The selection of a clinical device will prompt the system to distribute that device to all trial subjects. The user also selected consumer devices 1, 3, and 7. When trial subjects log into the application they will be asked if they have one of those three devices, and if they wish to allow the app to collect data from that device for the purposes of the clinical trial. The fourth column contains all backend documentation available, with the documents deemed relevant preselected. The user can select additional documentation to include from this screen.

FIG. 10 illustrates a usability database. The illustrated table is for patient application #123 and the data is collected from subject mobile devices and the averages for time spent, number of clicks, and completion percentage are calculated by the real world use module and stored in columns three, four, and five. The first column contains the name of the element/question/screen/login. The second column contains the number of data points used to calculate the averages in columns three, four and five. The number of data points is used to determine if the sample size is large enough to determine that the data in columns three, four and five are statistically significant, and should be acted upon.

FIG. 11 illustrates a building database. This first column as shown has the identification number for an application that was constructed using this system. The rest of the columns are all of the elements available from the element database and what order they appear in the application specified in the first column.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method for clinical trial configuration, the method comprising:
storing an element database in memory, wherein the element database includes information regarding a plurality of application elements;
identifying a set of one or more required application elements and optional application elements from the element database in real time based on one or more responses to a series of questions posited to a user device over a communication network that includes questions pertaining to a type of clinical trial, wherein each response determines a next question in the series, wherein the required application elements are necessary to comply with one or more application rules associated with the type of clinical trial;
receiving a selection of a set of application elements among the required application elements and optional application elements;
identifying that one or more of the required application elements and optional application elements are missing from the selected set of application elements based on analysis of the one or more responses and the selected set of application elements;
generating one or more recommendations regarding options for the required application elements and the optional application elements identified as missing from the selected set, the recommended options displayed within a graphic user interface for approval by the user device; and
constructing the application as an arrangement of application elements that include the selected set of elements and one or more of the required application elements and the optional application elements that have been identified as missing from the selected set and corresponding to a set of the recommended options displayed within the graphic user interface that have been approved by the user device.

2. The method of claim 1, further comprising storing a completion percentage as to whether each of the application element is completed by one or more mobile device users in a use database in the memory for each of the application elements based on the information from mobile devices, wherein the use database is accessible to the user device.

3. The method of claim 1, wherein the questions posited to the user device pertain to a type of clinical trial, and wherein identifying that the one or more application elements are missing from the selected set of application elements includes:
identifying one or more elements required to comply with one or more applicable rules associated with the type of clinical trial; and
comparing the required elements to the selected application elements, wherein generating the one or more recommendations is based on the comparison.

4. The method of claim 1, wherein the questions posited to the user device pertain to a type of clinical trial, and wherein identifying that the one or more application elements are missing from the selected set of application elements includes:
identifying one or more optional elements that are relevant to the type of clinical trial indicated by the one or more responses; and
comparing the optional elements to the selected application elements, wherein generating the one or more recommendation is based on the comparison.

5. The method of claim 1, further comprising positing additional questions to the user device when the user device rejects one or more of the recommendations regarding the missing application elements.

6. The method of claim 1, further comprising:
  identifying one or more documentations that correspond to the selected set of elements from a documentation database; and
  presenting the one or more documentations to the user device.

7. The method of claim 2, further comprising:
  identifying that the completion percentage of at least one of the application elements falls below a user-defined threshold; and
  generating an alert regarding the at least one application element associated with the completion percentage that falls below the user-defined threshold.

8. The method of claim 1, further comprising modifying at least one of the application elements, wherein modifying the at least one application element includes at least one of removing, replacing, changing color, and changing an arrangement of the application elements within the constructed application.

9. The method of claim 1, further comprising modifying at least one application element by:
  comparing an average time to complete the arrangement of application elements with a completion time threshold;
  comparing a number of the application elements that are arranged on one screen by the arrangement with an element number threshold; and
  separating the application elements within the arrangement into two or more screens when the number of the application elements that are arranged on the one screen exceeds the element number threshold and the average time to complete the arrangement of application elements exceeds the completion time threshold.

10. The method of claim 1, further comprising modifying at least one application element by:
  identifying a click pattern based on a location and a sequence of clicks on one screen that includes the arrangement of application elements; and
  rearranging the arrangement of application elements based on the location and the sequence of clicks, the arrangement being rearranged to correspond to the identified click pattern.

11. The method of claim 1, further comprising sending an alert to the user device when a completion percentage of the arrangement of application elements on one screen is below a completion percentage threshold.

12. A system for clinical trial configuration, the system comprising:
  a memory that stores an element database, wherein the element database includes information regarding a plurality of application elements; and
  a processor coupled to the memory, wherein the processor executes instructions to:
    identify a set of one or more required application elements and optional application elements from the element database based on one or more responses to a series of questions posited to a user device over a communication network that includes questions pertaining to a type of clinical trial, wherein each response determines a next question in the series, wherein the required application elements are necessary to comply with one or more application rules associated with the type of clinical trial;
    receive a selection of a set of application elements among the required application elements and optional application elements;
    identify that one or more of the required application elements and the optional application elements are missing from the selected set of application elements based on analysis of the one or more responses and the selected set of application elements;
    generate one or more recommendations regarding options for the required application elements and the optional application elements identified as missing from the selected set, the recommended options displayed within a graphic user interface for approval by the user device; and
    construct the application as an arrangement of application elements that include the selected set of elements and one or more of the required application elements and the optional application elements identified as missing from the selected set and corresponding to a set of the recommended options displayed within the graphic user interface that have been approved by the user device.

13. The system of claim 12, further comprising storing a completion percentage as to whether each of the application element is completed by one or more mobile device users in a use database in the memory for each of the application elements based on the information from mobile devices, wherein the use database is accessible to the user device.

14. The system of claim 12, wherein the questions posited to the user device pertain to a type of clinical trial, and wherein the processor identifies that the one or more application elements are missing from the selected set of application elements by:
  identifying one or more elements required to comply with one or more applicable rules associated with the type of clinical trial; and
  comparing the required elements to the selected application elements to identify that the one or more application elements are missing from the selected set of application elements.

15. The system of claim 12, wherein the questions posited to the user device pertain to a type of clinical trial, and wherein the processor identifies that the one or more applications elements are missing from the selected set of application elements by:
  identifying one or more optional elements wherein the optional elements are elements relevant to the type of the clinical trial based on the one or more responses to questions; and
  comparing the optional elements to the selected application elements to identify that the one or more applications are missing from the selected set of application elements.

16. The system of claim 12, further comprising a communication interface that posits additional questions to the user device when the user device rejects one or more of the recommendations regarding the missing application elements.

17. The system of claim 12, wherein the processor further identifies one or more documentations that correspond to the selected set of elements from a documentation database and presents the one or more documentations to the user device.

18. The system of claim 13, wherein the processor further:
  identifies that the completion percentage of at least one of the application elements falls below a user-defined threshold; and
  generates an alert regarding the at least one application element associated with the completion percentage that falls below the user-defined threshold.

19. The system of claim 12, wherein the processor further modifies at least one application element by at least one of removing, replacing, changing color, and changing an arrangements of the application elements within the constructed application.

20. The system of claim 12, wherein the processor further modifies at least one application element by:
- comparing an average time to complete the arrangement of application elements with a completion time threshold;
- comparing a number of the application elements that are arranged on one screen by the arrangement with an element number threshold; and
- separating the application elements within the arrangement into two or more screens when the number of the application elements that are arranged on the one screen exceeds the element number threshold and the average time to complete the arrangement of application elements exceeds the completion time threshold.

21. The system of claim 12, wherein the processor further modifies at least one application element by:
- identifying a click pattern based on a location and a sequence of clicks on one screen that includes the arrangement of application elements; and
- rearranging the arrangement of application elements on the screen based on the location and the sequence of clicks, the arrangement being rearranged to correspond to the identified click pattern.

22. The system of claim 12, further comprising a communication interface that sends an alert to the user device when a completion percentage of the arrangement of application elements on one screen is below a completion percentage threshold.

23. A non-transitory computer readable storage medium, having embodied thereon a program executable by a processor to perform a method for clinical trial configuration, the method comprising:
- storing an element database in memory, wherein the element database includes information regarding a plurality of application elements;
- identifying a set of one or more required application elements and optional application elements from the element database in real time based on one or more responses to a series of questions posited to a user device over a communication network that includes questions pertaining to a type of clinical trial, wherein each response determines a next question in the series, wherein the required application elements are necessary to comply with one or more application rules associated with the type of clinical trial;
- receiving a selection of a set of application elements among the required application elements and optional application elements;
- identifying that one or more required application elements and optional application elements are missing from the selected set of application elements based on analysis of the one or more responses and the selected set of application elements;
- generating one or more recommendations regarding options for the required application elements and the optional application elements identified as missing from the selected set, the recommended options displayed within a graphic user interface for approval by the user device; and
- constructing the application as an arrangement of application elements that include the selected set of elements and one or more of the required application elements and the optional application elements identified as missing from the selected set and corresponding to a set of the recommended options displayed within the graphic user interface that have been approved by the user device.

* * * * *